US006087115A

United States Patent [19]
Gershengorn et al.

[11] Patent Number: 6,087,115
[45] Date of Patent: Jul. 11, 2000

[54] METHODS OF IDENTIFYING NEGATIVE ANTAGONISTS FOR G PROTEIN COUPLED RECEPTORS

[75] Inventors: Marvin C. Gershengorn; Leandros Arvanitakis, both of New York; Elizabeth Geras-Raaka, Dobbs Ferry, all of N.Y.; Ethel Cesarman, Hoboken, N.J.

[73] Assignee: Cornell Research Foundation, Inc., Ithaca, N.Y.

[21] Appl. No.: 08/785,928

[22] Filed: Jan. 22, 1997

[51] Int. Cl.[7] .................. G01N 33/566; C12N 15/39; C12N 5/10; C07K 14/03
[52] U.S. Cl. .................. 435/7.21; 435/6; 435/7.2; 435/8; 435/69.1; 435/325; 435/365; 435/252.3; 435/254.11; 536/23.72; 536/24.1; 536/23.1; 530/350
[58] Field of Search .................. 435/6, 7.21, 7.2, 435/8, 69.1, 325, 365, 252.3, 254.11; 530/350; 536/23.72, 24.1, 23.1

[56] References Cited

U.S. PATENT DOCUMENTS

| | | | |
|---|---|---|---|
| 5,087,564 | 2/1992 | Mai et al. | 435/69.7 |
| 5,384,243 | 1/1995 | Gutkind et al. | 435/6 |
| 5,385,831 | 1/1995 | Mulvihill et al. | 435/69.1 |
| 5,403,484 | 4/1995 | Ladner et al. | 435/235.1 |

(List continued on next page.)

OTHER PUBLICATIONS

Heinflink et al., Molecular Endocrinology, 9, 1455–1460, 1995.
Himmler et al., Journal of Receptor Research, 13, 79–94, 1993.
Eggerickx et al., Biochem. J., 309, 837–843, 1995.
Cesarman et al., "Kaposi's Sarcoma–Associated Herpesvirus Contains G Protein–Coupled Receptor and Cyclin D Homologs Which Are Expressed in Kaposi's Sarcoma and Malignant Lymphoma," *Journal of Virology*, 70(11):8218–8223(1996).
Burbach et al., "The Structure of Neuropeptide Receptors," *European Pharm –Mol. J. Pharm. Sec.*, 227:1–18 (1992).
Chen et al., "Tethered Ligand Library for Discovery of Peptide Agonists," *J.Biol. Chem.*, 270(40):23398–23401 (1995).
Perez et al., Human Formyl Peptide Receptor Ligand Binding Domain(s), *J. Biol. Chem.*, 269(36):22485–22487 (1994).
Horvat et al., "The Functional Thrombin Receptor is Associated with the Plasmalemma and a Large Endosomal Network in Cultured Umbilical Vein Endothelial Cells," *J. Cell Science*, 106:1155–1164 (1995).
Stroop et al., "Chimeric Human Calcitonin and Glucagon Receptors Reveal Two Dissociable Calcitonin Interaction Sites," *Biochemistry*, 34:1050–1057 (1995).
Price et al., "Functional Coupling of a Mammalian Somatostatin Receptor to the Yeast Pheromone Response Pathway," *Mol. and Cell. Biol.*, 15(11):6188–6195 (1995).

Tsou et al., "A β2RARE–*LacZ* Transgene Identifies Retinoic Acid–Mediated Transcriptional Activation in Distinct Cutaneous Sites," *Experimental Cell Research*, 214:27–34 (1994).
Tate et al., "Secreted Alkaline Phosphatase: An Internal Standard for Expression of Injected mRNAs in the *Xenopus oocyte*," FASEB J., 4:227–231 (1990).
Laakkonen et al., "A Refined Model of the Thyrotropin–Releasing Hormone (TRH) Receptor Binding Pocket. Novel Mixed Mode Monte Carlo/Stochastic Dynamics Simulations of the Complex between TRH and TRH Receptor," *Biochemistry*, 35(24):7651–7663 (1996).
Gundersen et al., "Neural Regulation of Muscel Acetylcholine Receptor ε–and α–Subunit Gene Promoters in Transgenic Mice," *J. Cell Biol.*, 123(6):1535–1544 (1993).
Heinflink et al., "A Constitutively Active Mutant Thyrotropin–Releasing Hormone Receptor Is Chronically Down–Regulated in Pituitary Cells: Evidence Using Chlordiazepoxide as a Negative Antagonist," *Mol. Endocrin.*, 9(11):1455–1460 (1995).
Hersh et al., "Modulation of Gene Expression after Replication–Deficient, Recombinant Adenovirus–Mediated Gene Transfer by the Product of a Second Adenovirus Vector," *Gene Therapy*, 2:124–131 (1995).
Yan et al., "Multiple Regions of NSR1 Are Sufficient for Accumulation of a Fusion Protein within the Nucleolus," *J. Cell Biol.*, 123(5):1081–1091 (1993).
Tapparelli et al., "Structure and Function of Thrombin Receptors," *TiPS*, 14:426–428 (1993).
Gershengorn et al., "Molecular and Cellular Biology of Thyrotropin–Releasing Hormone Receptors," *Physiological Reviews*, 76(1):175–191 (1996).
Cascieri et al., "Molecular Characterization of a Common Binding Site for Small Molecules Within the Transmembrane Domain of G–Protein Coupled Receptors," *J. Pharma. and Toxicol. Methods*, 33:179–185 (1995).

*Primary Examiner*—Lorraine Spector
*Assistant Examiner*—Claire M. Kaufman
*Attorney, Agent, or Firm*—Nixon Peabody LLP

[57] ABSTRACT

The present invention is directed to a constitutively active G protein coupled receptor of human herpesvirus 8, as well as a method of identifying negative antagonists of a constitutively active G protein coupled receptor. The method comprises co-expressing in a host cell a constitutively active G protein coupled receptor and a reporter protein, wherein expression of the reporter protein is controlled by a promoter responsive to a signalling pathway activated by the constitutively active G protein coupled receptor; exposing the host cell to a test substance; and determining a level of reporter protein activity, wherein the level of reporter protein activity indicates effectiveness of the test substance as a negative antagonist of the constitutively active G protein coupled receptor. The invention further provides a method of preventing tumor formation or cell proliferation caused by a constitutively active G protein coupled receptor. This method comprises administering an amount of the negative antagonist so identified to a subject in an amount effective to prevent tumor formation or cell proliferation.

7 Claims, 5 Drawing Sheets

U.S. PATENT DOCUMENTS

| | | | |
|---|---|---|---|
| 5,436,128 | 7/1995 | Harpold et al. | 435/6 |
| 5,462,856 | 10/1995 | Lerner et al. | 435/7.21 |
| 5,476,781 | 12/1995 | Moyer et al. | 435/240.2 |
| 5,482,835 | 1/1996 | King et al. | 435/6 |
| 5,498,530 | 3/1996 | Schatz et al. | 435/69.1 |
| 5,506,102 | 4/1996 | McDonnell | 435/6 |
| 5,508,384 | 4/1996 | Murphy et al. | 530/324 |
| 5,516,889 | 5/1996 | Hollenberg et al. | 530/317 |
| 5,521,295 | 5/1996 | Pacifici et al. | 536/23.4 |
| 5,908,773 | 9/1996 | Cesarman et al. | |
| 5,948,676 | 10/1996 | Chang et al. | |

METHODS OF IDENTIFYING NEGATIVE ANTAGONISTS FOR G PROTEIN COUPLED RECEPTORS

The subject matter of this application was made with support from the United States Government under National Institutes of Health Grant Nos. DK43036 and DK46652.

FIELD OF THE INVENTION

The present invention relates to a constitutively active G protein coupled receptor of human herpesvirus 8. The invention further relates to a method of identifying negative antagonists of constitutively active G protein coupled receptors, and to a method of preventing tumor formation or cell proliferation caused by the constitutively active G protein coupled receptor by administering an effective amount of the identified negative antagonist.

BACKGROUND OF THE INVENTION

Throughout this application various publications are referenced, many in parenthesis. Full citations for these publications are provided at the end of the Detailed Description of the Invention. The disclosures of these publications in their entireties are hereby incorporated by reference in this application.

The family of guanine nucleotide-binding (G) protein-coupled receptors (GPCRs) has been estimated to be comprised of as many as 2,000 members, fully more than 1.5% of all the proteins encoded in the human genome, that are thought to regulate function of virtually every cell in the body. Furthermore, it has been estimated that more than 50% of the drugs in use clinically in humans at the present time are directed at GPCRs.

In general, GPCRs require agonist binding for activation. Constitutive (or agonist-independent) signalling activity in mutant receptors has been well documented but only a few GPCRs have been shown to exhibit agonist-independent activity in the wild type (or native) form. For example, native dopamine D1B and prostaglandin EP1b receptors have been found to possess constitutive activity (Tiberi and Caron 1994; Hasegawa et al. 1996). A number of GPCRs, for example, receptors for thyroid-stimulating hormone (Vassart et al. 1995), have been found to be mutated to exhibit agonist-independent activity and cause disease in humans. Experimentally, several single amino acid mutations have produced agonist independent activity. β2 and α2 adrenergic receptors, for example, mutated at single sites in the third cytoplasmic loop show constitutive activity (Ren et al. 1993; Samama et al. 1994). In some cases, a large deletion mutation in the carboxy tail or in the intracellular loops of GPCRs has led to constitutive activity. For example, in the thyrotropin releasing hormone receptor a truncation deletion of the carboxyl terminus renders the receptor constitutively active (Nussenzveig et al. 1993; Matus-Leibovitch et al. 1995) and a smaller deletion in the second extracellular loop of the thrombin receptor causes constitutive activity (Nanevicz et al. 1995) also.

The finding that certain receptors exhibit constitutive activity has led to a modification of traditional receptor theory (Samama et al. 1993). It is now thought that receptors can exist in at least two conformations, an inactive conformation (R) and an activated conformation (R*), and that an equilibrium exists between these two states that markedly favors R over R* in the majority of receptors. In some native receptors and in the mutants described above, it has been proposed that in the absence of agonist there is a shift in equilibrium that allows a sufficient number of receptors to be in the active R* state to initiate signalling.

As many more GPCRs with constitutive activity are found, both native as well as mutated receptors, a newly recognized class of drugs termed negative antagonists (or inverse agonists) will become important therapeutic agents. Negative antagonism is demonstrated when a drug binds to a receptor that exhibits constitutive activity and reduces this activity. Negative antagonists appear to act by constraining receptors in an inactive state (Samama et al. 1994). Although first described in other receptor systems (Schutz and Freissmuth 1992), negative antagonism has been shown to occur with guanine nucleotide-binding (G) protein-coupled receptors (GPCRs), for example, opoid (Costa and Herz 1989; Costa et al. 1992), $\beta_2$-adrenergic (Samama et al. 1994; Pei et al. 1994; Chidiac et al. 1994), serotonin type 2C (Barker et al. 1994), bradykinin (Leeb-Lundberg et al. 1994), and D1B dopamine receptors (Tiberi and Caron 1994). Thus, a technology for identifying negative antagonists of native and mutated GPCRs has important predictable as well as not yet realized pharmaceutical applications. Furthermore, because constitutively active GPCRs are tumorigenic, the identification of negative antagonists for these GPCRs can lead to the development of anti-tumor and/or anti-cell proliferation drugs.

SUMMARY OF THE INVENTION

To this end, the subject invention provides a constitutively active G protein coupled receptor of human herpesvirus 8, and a method of identifying negative antagonists of a constitutively active G protein coupled receptor. The method comprises co-expressing in a host cell a constitutively active G protein coupled receptor and a reporter protein, wherein expression of the reporter protein is controlled by a promoter responsive to a signalling pathway activated by the constitutively active G protein coupled receptor; exposing the host cell to a test substance; and determining a level of reporter protein activity, wherein the level of reporter protein activity indicates effectiveness of the test substance as a negative antagonist of the constitutively active G protein coupled receptor.

The invention further provides a method of preventing tumor formation or cell proliferation in a subject caused by a constitutively active G protein coupled receptor. This method comprises identifying a negative antagonist of a constitutively active G protein coupled receptor; and administering to the subject an amount of the negative antagonist effective to prevent tumor formation or cell proliferation caused by the constitutively active G protein coupled receptor.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

The subject invention provides a constitutively active G protein coupled receptor of human herpesvirus 8.

The invention further provides a method of identifying negative antagonists of a constitutively active G protein coupled receptor. The method comprises co-expressing in a host cell a constitutively active G protein coupled receptor and a reporter protein, wherein expression of the reporter protein is controlled by a promoter responsive to a signalling pathway activated by the constitutively active G protein coupled receptor; exposing the host cell to a test substance; and determining a level of reporter protein activity, wherein the level of reporter protein activity indicates effectiveness of the test substance as a negative antagonist of the constitutively active G protein coupled receptor.

The constitutively active G protein coupled receptor can be any such receptor which one desires to turn off. For example, GPCRs which are tumorigenic or which cause cells to proliferate could be of interest for application of the method of the subject invention. By identifying negative antagonists of such GPCRs, the negative antagonists could be used to turn off the GPCR and thereby eliminate the GPCR's tumorigenic or cell proliferative effects. An example of such a constitutively active GPCR is the GPCR of human herpesvirus 8 (HHV 8) (also known as Kaposi's sarcoma associated herpesvirus or KSHV) (Cesarman et al. 1996).

Having identified a GPCR of interest, the signalling pathway activated by the GPCR is identified and a promoter responsive to the signalling pathway is selected. Such a "responsive" promoter will only promote expression of a downstream gene if the GPCR is functioning (i.e., signalling through its pathway). GPCRs use various signalling pathways, including cyclic AMP pathways and protein kinase C pathways. Suitable promoters for use with such GPCRs are cyclic AMP-responsive promoters and protein kinase C-responsive promoters, respectively. For a review of the cyclic AMP signalling pathway see Habener 1995, and for a review of the protein kinase C signalling pathway see Gershengorn and Perlman 1995.

A reporter protein is then chosen. The activity levels of the reporter protein will indicate the levels of GPCR signalling, since the reporter protein will only be expressed if the GPCR is signalling through its pathway to which the selected promoter is responsive. A reporter protein should be chosen which is not generally expressed in the host cell to be utilized for co-expression, to eliminate any false indications of GPCR signalling. A suitable reporter protein, as disclosed in the following examples, is the firefly luciferase gene. The activity of this reporter protein can be readily assayed using a luminescent assay. Other reporter proteins could also be readily used in the method of the subject invention, such as β-galactosidase and growth hormone.

Various host cells can be utilzed in the method of the subject invention. The choice of a host cell is based on several factors, including the absence of endogenous expression of the reporter protein in the host cell, presence of the GPCR signalling pathway in the host cell, and capability of co-expressing the GPCR and the reporter protein in the host cell. For the analysis of human GPCRs, mammalian cells are preferred, such as COS cells.

Generally the co-expression of the constitutively active G protein coupled receptor and the reporter protein in the host cell will involve introduction of two constructs into the host cell. The first construct is a nucleic acid molecule encoding the G protein coupled receptor under the control of suitable regulatory molecules for expression of the GPCR in the host cell. The second construct is a nucleic acid molecule encoding the reporter protein under the control of the promoter responsive to the signalling pathway of the GPCR. Each construct can be provided in the form of a plasmid, or a single plasmid comprising both constructs could be used. Techniques for introducing the construct(s) into the host cells may involve the use of expression vectors (such as plasmids and viruses) which comprise the nucleic acid molecule encoding the construct(s). DNA encoding the construct can be injected into the nucleus of a host cell or transformed into the host cell using a suitable vector, or mRNA encoding the construct can be injected directly into the host cell, in order to obtain expression of the GPCR and the reporter protein in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (e.g. dextran) to which a positively charged chemical group (e.g. diethylaminoethyl ("DEAE")) has been coupled. The DNA sticks to the DEAE-dextran via its negatively charged phosphate groups. These large DNA-containing particles, in turn, stick to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may some-times destroy or damage DNA). DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Further methods for introducing nucleic acid molecules into cells involve the use of viral vectors. Since viral growth depends on the ability to get the viral genome into cells, viruses have devised clever and efficient methods for doing it. Various viral vectors have been used to transform mammalian cells, such as vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Various test substances can be screened for their effectiveness as negative antagonists of a constitutively active GPCR. Test substances can be, for example, traditional chemical compounds (such as benzodiazepines) or peptides. Any suitable test substance can be screened in the subject method, as long as the host cell can be exposed to the test substance.

Having thus identified negative antagonists of a constitutively active G protein coupled receptor, and knowing that constitutively active G protein coupled receptors cause tumor formation or cell proliferation, the invention further provides a method of preventing tumor formation or cell proliferation in a subject caused by a constitutively active G protein coupled receptor. The method comprises identifying a negative antagonist of a constitutively active G protein coupled receptor (as discussed above); and administering to the subject an amount of the negative antagonist effective to prevent tumor formation or cell proliferation caused by the constitutively active G protein coupled receptor. In one embodiment, the tumor formation or cell proliferation is caused by a constitutively active G protein coupled receptor of a virus such as human herpesvirus 8.

The following examples relate to the identification of a constitutively active GPCR of human herpesvirus 8, and the assaying of the GPCR activity by co-expressing a reporter protein under the control of a promoter responsive to the GPCR signalling pathway. By then exposing the host cell to a test substance, the effectiveness of the test substance as a negative antagonist of the constitutively active GPCR can be determined (by determining the effect of the test substance on reporter protein activity). The identified negative antagonists could serve as probes to determine the role of agonist-independent HHV8 GPCR activity in diseases associated with HHV 8 infections or as lead compounds for drugs (Navia and Murcko 1992) if a role for HHV8 GPCR in a disease process(es) is demonstrated. In particular, because constitutively active GPCRs have been found to be tumorigenic in mice (Young et al. 1986) or to mediate proliferation or transformation of cells infected with HHV 8 (Julius et al. 1989; Allen et al. 1991; Gutkind et al. 1991), these negative antagonists could lead to the development of anti-tumor drugs.

MATERIALS AND METHODS

Competition binding. The coding sequence of KSHV GPCR was cleaved from its original subcloning plasmid (Cesarman et al. 1996) by digestion with NcoI and inserted into the EcoRV site of the eukaryotic expression vector pcDNA3.1(+) (Invitrogen), producing the pcKSHV GPCR used for expression in mammalian cells. COS-1 cells (American Type Culture Collection) were grown in 100 mm petri dishes in Dulbecco's modified Eagle's medium (DMEM; GIBCO-BRL) with 5% Nu-Serum (Collaborative Research) in a humidified incubator in an atmosphere of 5% $CO_2$ at 37° C. DEAE-dextran transfections were carried out as previously described (Nussenzveig et al. 1994) COS-1 cells were transfected with 10 mg/ml of pcKSHV GPCR and tested for IL-8 binding 48 hrs post-transfection. Approximately 100,000 cells per well (in 12-well plates) were washed with Hank's balanced salt solution (HBSS) containing 25 mM HEPES, pH 7.4 (GIBCO-BRL). Between 0.3 and 0.5 nM $^{125}$I-IL-8 (DuPont-NEN) in the absence or presence of various concentrations of unlabelled chemokines was added and binding was allowed to proceed at 4° C. for 2 hrs with gentle rocking. The binding buffer contained bovine serum albumin (BSA; 1 mg/ml), bacitracin (1 mg/ml), and phenyl methyl sulphonyl fluoride (PMSF; 1 mM). Assays were terminated by aspirating the binding buffer, washing three times with chilled HBSS and solubilizing the cells with 0.4 N NaOH. An aliquot of this solution was counted in a gamma counter and the data expressed as percent of maximum bound. Binding and dose-response curves were analyzed using Prism software (GraphPad, Inc.).

Inositol phosphate accumulation. COS-1 cells were transfected with pcKSHV GPCR or plasmids encoding human IL-8 receptor types A or B and either $Ga_{16}$ or $Ga_{15}$ (Wu et al. 1993). All transfection cocktails were supplemented to contain equal total plasmid DNA by the addition of appropriate amounts of vector (pcDNA3.1). Twenty four hrs following transfection, cells were harvested and reseeded in 12-well plates in DMEM with 10% Nu serum and 1 mCi/ml myo-[$^3$H]inositol (DuPont-NEN), and maintained in culture as before for an additional 24 hrs. After removing the culture media and rinsing the cells, cells were incubated in HBSS containing 25 mM HEPES, pH 7.4 with 10 mM LiCl in the absence or presence of human recombinant IL-8 (R&D Systems) at 0.25 mg/ml. Cells were harvested after 90 min or other time points, and IP accumulation measured using ion exchange chromatography as described previously (Straub et al. 1990).

Luciferase assay. Cells were transfected with increasing amounts of pcKSHV-GPCR (0.003 to 0.100 mg/ml) and 5 mg/ml pAP1-fos-LUC (Schadlow et al. 1992), supplemented to contain equal total plasmid DNA by the addition of appropriate amounts of vector (pcDNA3.1). Cells were washed with phosphate-buffered saline (PBS) and lysed with 0.5 ml/10 cm dish of lysis buffer (25 mM GlyGly, 15 mM $MgSO_4$, 4 mM EGTA, 1 mM dithiothreitol (DTT), 1% Triton X-100, pH 7.8). Cell extracts were diluted 1:10 or 1:20 in reaction buffer (25 mM GlyGly, 15 mM $MgSO_4$, 4 mM EGTA, 1 mM DTT, 15 mM $KH_2PO_4$, 2 mM ATP, pH 7.8), combined with equal volumes of 0.4 mM luciferin in reaction buffer and luminescence measured for 10 sec.

Cell proliferation assay. "Normal rat kidney" fibroblasts (NRK-49F; ATCC) were seeded at $2\times10^5/100$ mm dish, grown in DMEM with 10% fetal calf serum, and transfected with control vector. (20 mg/plate), pcKSHV GPCR (20 mg/plate) or pRas-Zip (10 mg/plate; positive control) (Dotto et al. 1985) using the calcium phosphate method as previously described (Loyter et al. 1982). Cells were harvested 24 hrs post-transfection and seeded at a density of 5,000 cells/100 mm dish in DMEM supplemented with either 10% calf serum or fetal calf serum. On day 5 post-transfection, cells were photographed for qualitative assessment (Nikon inverted phase microscope) and then trypsinized to determine total cell number using a hemocytometer.

EXAMPLE I

Kaposi's sarcoma-associated herpesvirus (KSHV)/human herpesvirus 8 (HHV 8) is a recently described virus consistently present in Kaposi's sarcoma (KS) (Chang et al. 1994; Moore and Chang 1995) and primary effusion (body cavity-based) lymphomas (PEL) (Cesarman et al. 1995) which are malignancies occurring frequently, but not exclusively, in AIDS patients. KSHV is a gammaherpesvirus with homology to Herpesvirus Saimiri (HVS) and Epstein-Barr virus (EBV) (Chang et al. 1995; Moore et al. 1996), both of which are viruses capable of transforming lymphocytes (Roizman 1996). Cloning of a viral genome fragment revealed the presence of an open reading frame encoding a putative G protein-coupled receptor (KSHV GPCR) (Cesarman et al. 1996) that is homologous to a GPCR encoded by HVS (Nicholas et al. 1992; Ahuja and Murphy 1993) and to human interleukin 8 (IL-8) receptors (Holmes et al. 1991; Murphy and Tiffany 1991). In the studies that follow, it is shown that KSHV GPCR is a bona fide signaling receptor with constitutive (agonist-independent) activity via the phosphoinositide-1,4,5 inositoltrisphosphate-protein kinase C (PKC) cascade. Furthermore, KSHV GPCR is shown to stimulate cellular proliferation, making it a candidate viral oncogene. The nucleic acid and amino acid sequences of the HHV 8 GPCR are disclosed in co-pending, co-assigned U.S. Ser. No. 08/728,603, filed Oct. 10, 1996, the contents of which are hereby incorporated by reference.

Figure 1:
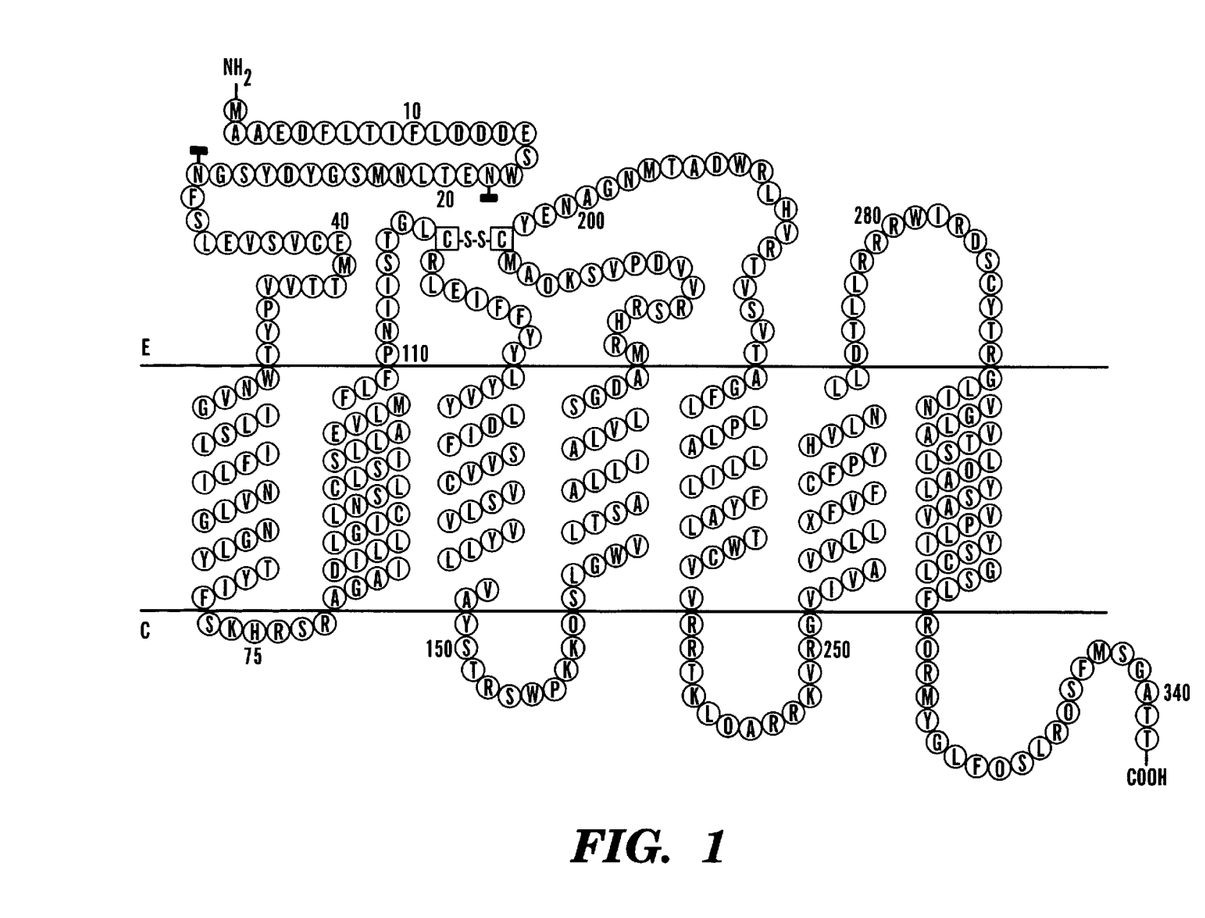
FIG. 1 illustrates the putative two-dimensional topology and amino acid sequence (SEQ. ID. No. 1) of the HHV 8 GPCR.

FIG. 1 illustrates the putative two-dimensional topology of HHV 8 GPCR. The top of the diagram represents the extracellular space (E), the middle portion represents the transmembrane (TM) domain, and the bottom portion represents the intracellular space (C). Each circle represents an amino acid residue designated by the single letter code.

As is evident, HHV 8 GPCR can be represented with the signature seven TM-spanning domains of all GPCRs. This, however, is not sufficient to classify this protein as a receptor. Moreover, it is lacking some of the residues that are highly conserved in GPCRs. The most relevant to this application relate to amino acid residues that have been found to be involved in activation of other GPCRs. For example, an Asp residue is usually present in putative TM-2 that has been shown to be critical for activation of a number of GPCRs (Baldwin 1994). There is an Asp at this position in both IL8-Rs but not in the GPCR in the Herpesvirus saimiri genome and not in HHV 8 GPCR. In HHV 8 GPCR this Asp has been replaced by Asn. A similar replacement of Asp by Asn in TM-2 is present in the receptor for gonadotropin-releasing hormone (GnRH) but in the GnRH receptor there is a complementary change of a highly conserved Asn in TM-7, which is in a Asn-Pro-Xaa-Xaa-Tyr motif (Baldwin 1993), to Asp (Zhou et al. 1994) that is not present in HHV 8 GPCR. It has been postulated that interactions between these two residues, Asp and Asn, may be necessary for receptor activation (van Rhee and Jacobson 1996). There is a Val at this position in TM-7 in HHV 8 GPCR that will not be able to form a hydrogen bond with the Asn in TM-2. The absence of this potential interaction between TM-2 and TM-7 may render HHV 8 GPCR constitutively active, but this cannot be predicted from the sequence.

Figure 2:
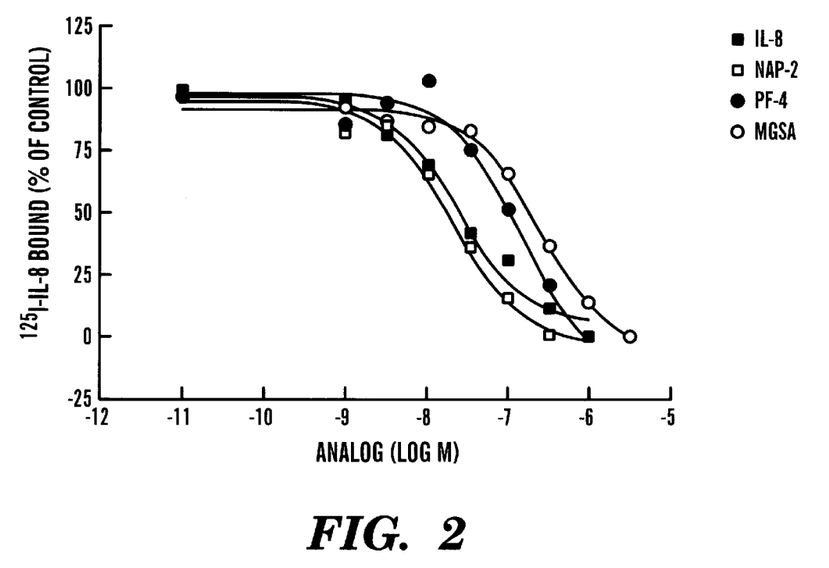
FIGS. 2 and 3 illustrate competition binding of human recombinant $^{125}$I-IL-8 by unlabelled chemokines to COS-1 cells transfected with pcKSHV GPCR (10 mg/ml). (2) C-X-C chemokines ($K_d$ or $K_i$): IL-8 (25 nM), NAP-2 (23 nM) PF-4 (150 nM) and MGSA (270 nM). (3) C-C chemokines ($K_d$ or $K_i$): I-309 (110 nM) and RANTES (520 nM). Data represent the mean of triplicate determinations in a representative of two experiments.
Figure 3:
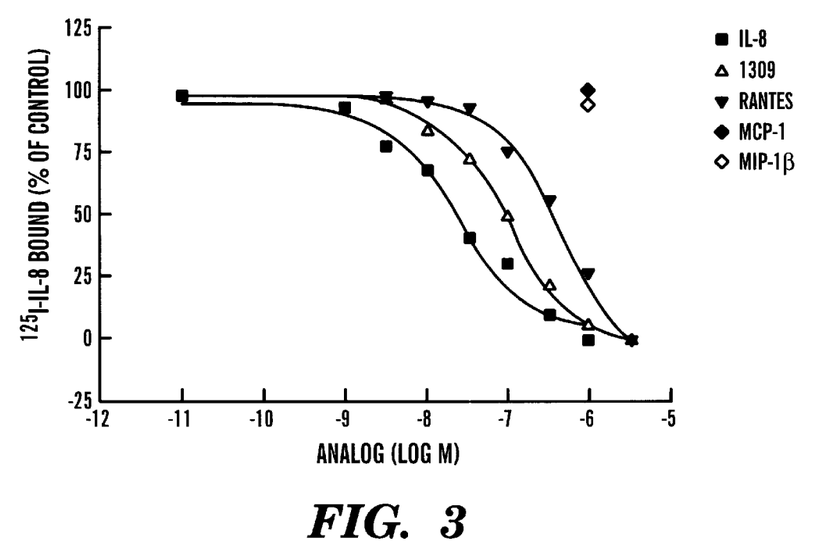

A number of experiments were performed to show that HHV 8 GPCR is a functioning receptor. To investigate whether the KSHV GPCR gene encodes a functional receptor, the KSHV GPCR was expressed in COS cells and a determination whether the receptor binds IL-8 and other chemokines was made. IL-8, which is a member of the family of C-X-C chemokines (Baggiolini et al. 1994), was chosen as radioligand because of the homology of KSHV GPCR to cellular IL-8 receptors. Furthermore, since KS lesions are sites of active inflammation and have been shown to produce IL-8 and other cytokines (Sciacca et al. 1994), it is possible that such areas could provide stimulatory signals for the KSHV GPCR. The binding characteristics of KSHV GPCR were investigated using $^{125}$I-IL-8 and various concentrations of other chemokines in a competition analysis. As shown in FIG. 2, KSHV GPCR binds IL-8 with an apparent equilibrium dissociation constant ($K_d$) of 30 nM, which is lower affinity than the values previously reported for binding of IL-8 to the human IL-8 receptor types A or B ($K_d$ of 0.8–1.0 nM) (Holmes et al. 1991; Murphy and Tiffany 1991). Since chemokine receptors may bind more than one ligand, several other C-X-C chemokines were tested, namely MGSA, NAP-2 and PF-4 (Baggiolini et al. 1994), and it was found that they also bind to KSHV GPCR (FIG. 2). Although chemokines of the C-C family do not bind to IL-8 receptors (Baggiolini et al. 1994), it was found that I-309 and RANTES bind to KSHV GPCR whereas MIP-1b and MCP-1 do not (FIG. 3). The rank order of binding was: IL-8=NAP-2>PF-4=I-309=MGSA>RANTES>>MIP-1b and MCP-1. Thus, KSHV GPCR exhibits binding characteristics of a chemokine receptor with affinity for a range of chemokines spanning the C-X-C and C-C families.

Figure 4:
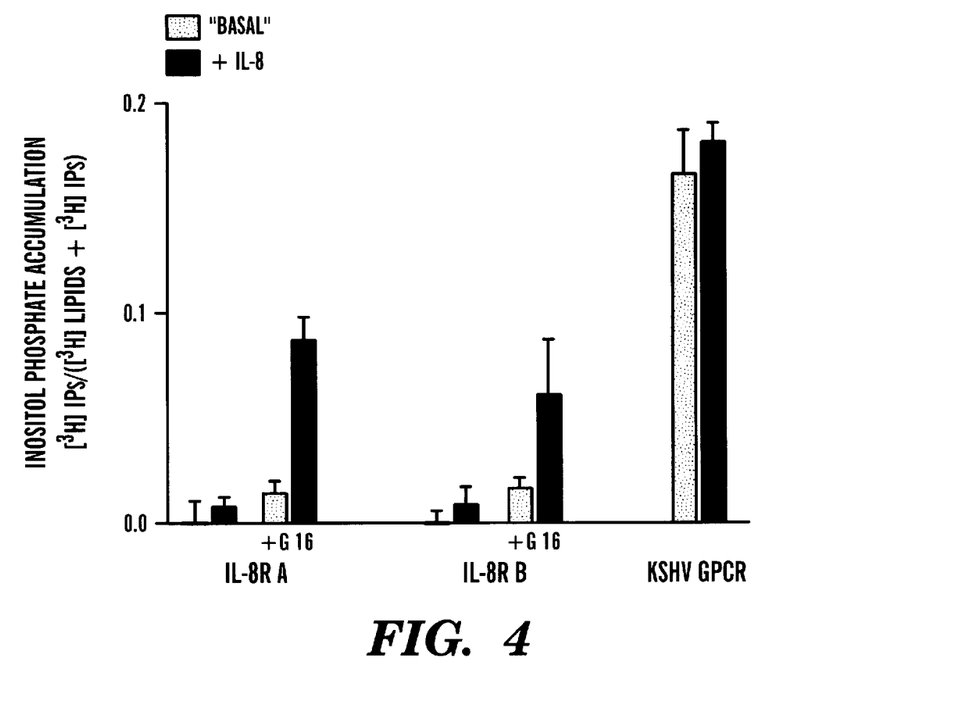
FIGS. 4 and 5 illustrate the characterization of inositol phosphate (IP) accumulation in COS-1 cells transfected with pcKSHV GPCR. (4) Comparison with COS-1 cells transfected with plasmids for human IL-8 receptors (type A or B; 10 mg/ml) in the presence or absence of plasmid encoding $G\alpha_{16}$ (2 mg/ml) after 90 minutes. (5) Time course in COS cells transfected with 10 mg/ml pcKSHV GPCR. Data represent the mean ± S.D. of triplicate determinations in a representative of three experiments; IP accumulation of mock-transfected, untreated cells has been subtracted from all points.
Figure 5:
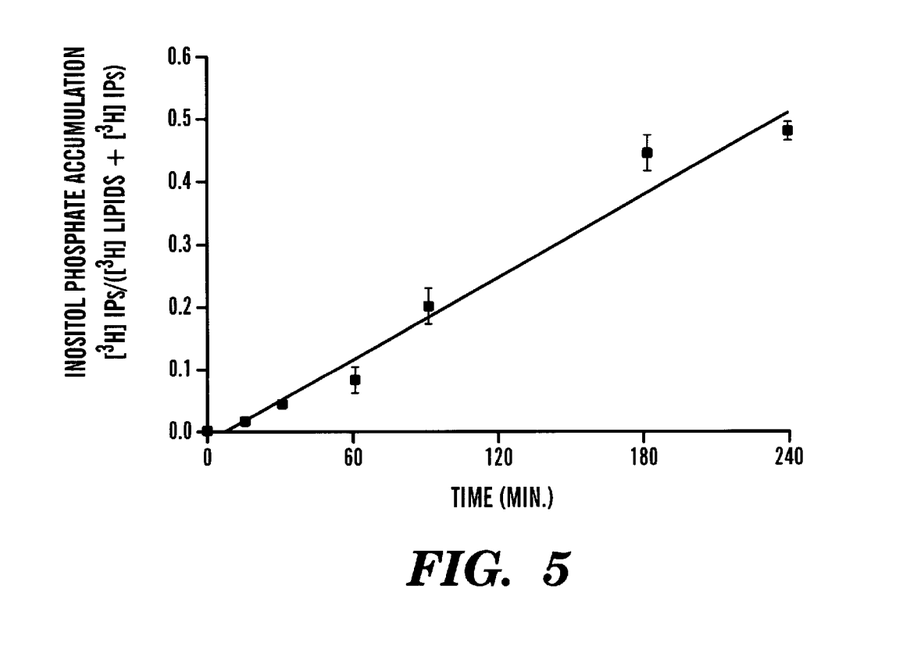
Figure 6:
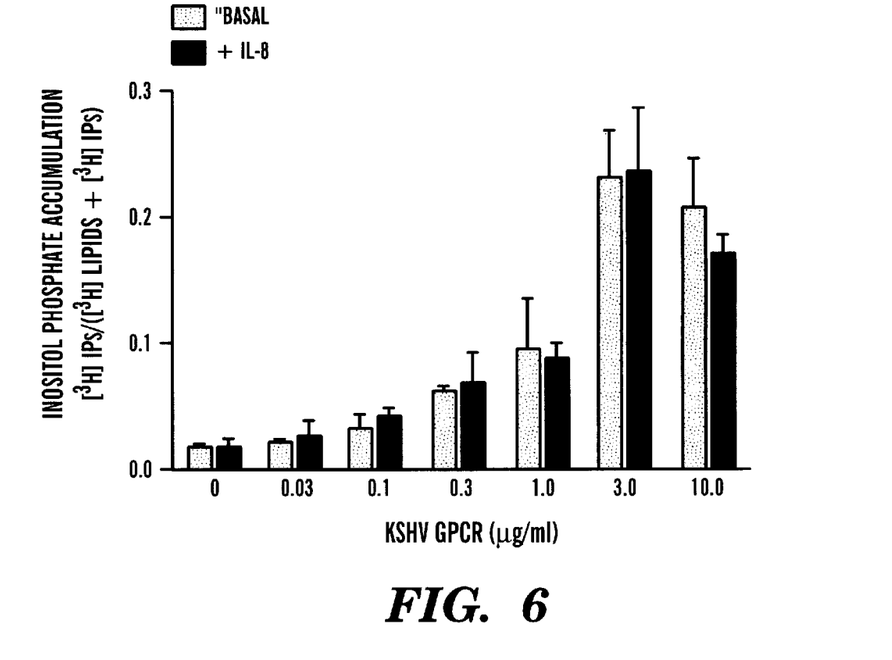
FIG. 6 illustrates the dose dependence of inositol phosphate (IP) accumulation in COS-1 cells after transfection with various amounts of pcKSHV GPCR (from 0.003 to 10 mg/ml), measured at 90 min. Data represent the mean ± S.D. of triplicate determinations in a representative of three experiments.

To assess whether KSHV GPCR is a signal transducing receptor, the formation of intracellular second messengers in COS cells transiently expressing KSHV GPCR was measured. Inositol phosphate (IP) accumulation was measured because IL-8 receptors signal via the phosphoinositide-IP-calcium/diacylglycerol-PKC cascade (Holmes et al. 1991; Murphy and Tiffany 1991). Stimulated IP formation can be measured in COS cells co-expressing IL-8 receptors and the a subunits of the heterotrimeric proteins $G_{16}$ ($Ga_{16}$) or $G_{15}$ ($Ga_{15}$) in the presence but not in the absence of IL-8 (Wu et al. 1993). In agreement with that report, little measurable accumulation of IPs in COS cells expressing IL-8 receptors in the absence or presence of IL-8 was found, unless $Ga_{16}$ or $Ga_{15}$ was cotransfected (FIG. 4). In cells expressing IL-8 receptors and $Ga_{16}$ or $Ga_{15}$, IL-8 stimulated IP formation. In contrast, and under these experimental conditions, cells transiently expressing KSHV GPCR showed IP accumulation which was higher than that obtained with human IL-8 receptors activated by IL-8. In cells transiently expressing KSHV GPCR, IP formation was elevated in the absence of added ligand and without co-expression of $Ga_{16}$ or $Ga_{15}$, and was not increased by IL-8 or any of the chemokines that showed binding to KSHV GPCR. There was a constant rate of IP accumulation for at least 4 hours (FIG. 5); IL-8 had no effect at any time point. Transfection of COS-1 cells with increasing amounts of plasmid encoding KSHV GPCR showed that IP accumulation was directly proportional to the amount of plasmid used for transfection (between 0.1 and 3 mg/ml plasmid) (FIG. 6). Again, there was no effect of IL-8 on IP accumulation at any level of KSHV GPCR expression. Thus, KSHV GPCR exhibits agonist-independent (or constitutive) activity in COS-1 cells. In contrast to IL-8 receptors, KSHV GPCR couples effectively to the G protein (s) endogenous in COS-1 cells. Since IP accumulation from the KSHV GPCR is resistant to pertussis toxin, this suggests that the receptor may signal through the Gq family of G-proteins.

Figure 7:
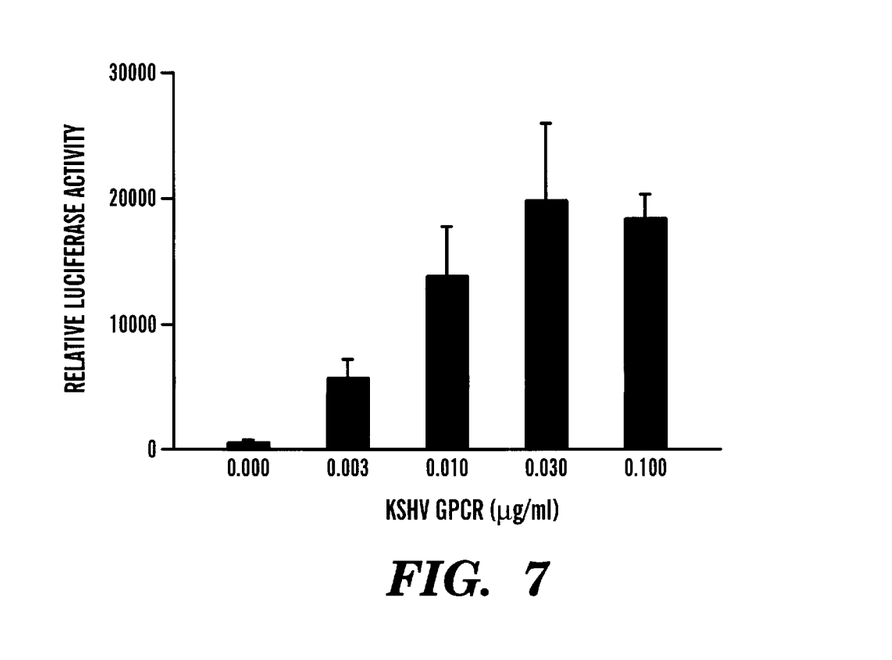
FIG. 7 illustrates the transcription of luciferase driven by a PKC-responsive promoter in COS-1 cells transfected with pcKSHV GPCR. Data represent the mean ± S.D. of triplicate determinations in a representative of three experiments.

To determine whether the constitutive signaling activity of KSHV GPCR leads to stimulation of downstream processes, the effect of basal second messenger formation on gene transcription was measured. A reporter gene, firefly luciferase, under the control of a PKC-responsive promoter containing an AP-1 binding motif (Schadlow et al. 1992) was used to measure activity of the diacylglycerol/PKC limb of the phosphoinositide signaling pathway. In these experiments, COS-1 cells were co-transfected with plasmid encoding KSHV GPCR and a plasmid containing a minimal promoter derived from the human c-fos gene to which a PKC-responsive element was inserted to drive luciferase transcription (Schadlow et al. 1992). As shown in FIG. 7, there was a direct relationship between the amount of plasmid encoding KSHV GPCR used for transfection and the level of luciferase activity. Thus, second messenger formation caused by the basal activity of KSHV GPCR is sufficient to induce gene transcription for a PKC-responsive promoter. This finding is important given the wide range of genes, including those for inflammatory and angiogenic agents, whose transcription is regulated by PKC-responsive promoters (Karin 1995). Of note is the observation that luciferase activity (FIG. 7) is stimulated at lower plasmid levels than IP accumulation (FIG. 6). This likely occurred because induction of gene transcription is a more amplified response occurring downstream of second messenger formation.

EXAMPLE II

Figure 8:
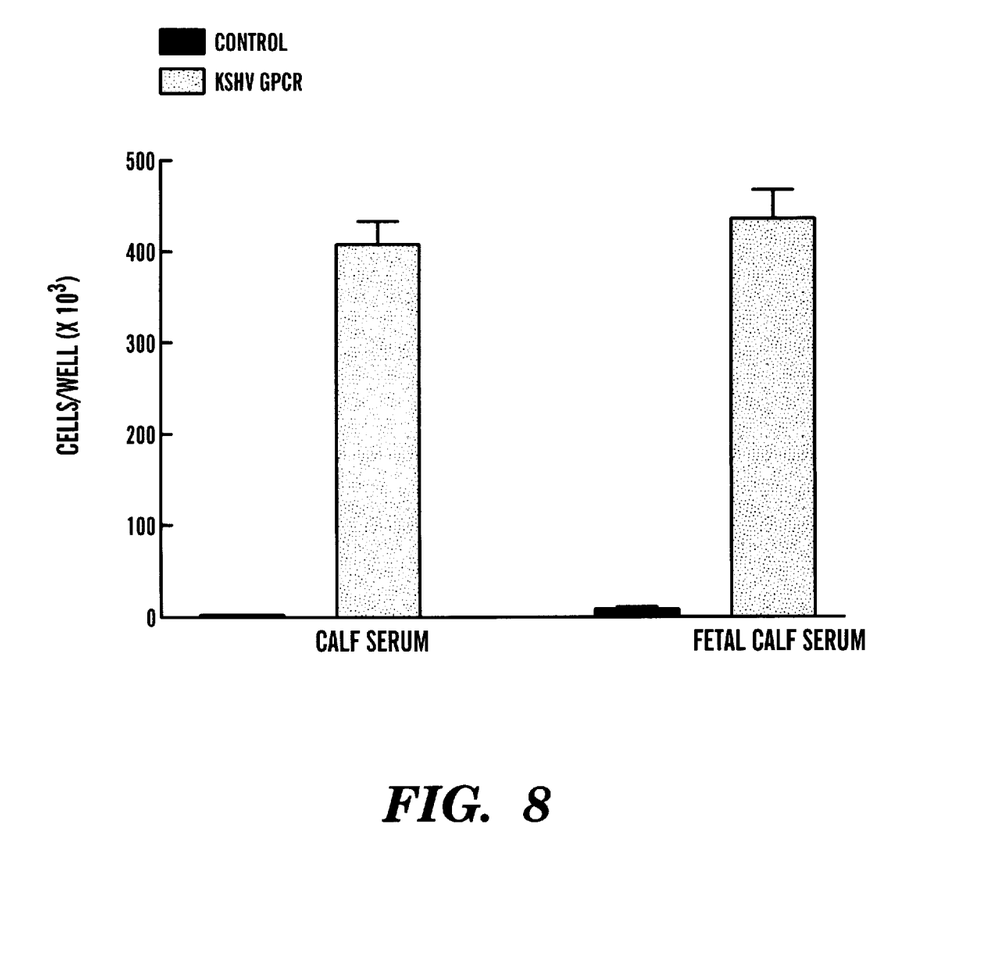
FIG. 8 illustrates cellular proliferation in NRK-49F cells transfected with control plasmid or pcKSHV GPCR. After 5 days in culture in medium supplemented with calf serum or fetal calf serum, transfected cells were trypsinized and counted. Cell counts; data represent the mean ± S.D. of triplicate culture dishes of three transfections.

To test whether the constitutive KSHV GPCR signaling activity affects cellular proliferation, NRK-49F cells were transiently transfected with plasmid encoding KSHV GPCR and monitored for proliferation as compared to cells transfected with control vector (negative control) or with a plasmid encoding the Ras oncogene (positive control) (Dotto et al. 1985). Culture dishes transfected with Ras-encoding plasmids contained more cells than control dishes within 24 to 48 hrs. As early as 72 hrs post-transfection, the KSHV GPCR transfectants exhibited increased cell number as compared to the control transfectants. This response was confirmed by phase contrast microscopy and quantified after 5 days in culture (FIG. 8). All clusters transfected with pcKSHV GPCR contained many more, closely apposed cells than clusters of cells transfected with control plasmid.

Since gammaherpesviruses cause tranformation (Roisman 1996) and GPCRs have been found to be oncogenic under some circumstances (Julius et al. 1989), it is possible that KSHV may be a transforming agent that acts, at least in part, through KSHV GPCR. This possibility is further strengthened by the specific association of KSHV with KS and PEL, and the fact that KSHV GPCR is expressed at the RNA level in both of these types of malignancies (Cesarman et al. 1996; Arvanitakis et al. 1996). These results have now demonstrated that KSHV GPCR is a bona fide receptor that signals constitutively via the phosphoinositide transduction pathway. Although it has an amino acid sequence that is homologous to IL-8 receptors, binds IL-8 with relatively high affinity and activates the same signal transduction cascade, KSHV GPCR has two characteristics that make it a more promiscuous receptor and one more likely to be involved in pathogenesis than IL-8 receptors. KSHV GPCR signals constitutively, that is, it does not require activation by an agonist(s) and is capable of coupling to a wider variety of G proteins than IL-8 receptors. Coupling of KSHV GPCR to G proteins other than $Ga_{16}$, as shown by signaling in COS cells that do not express this G protein, would allow KSHV GPCR to signal in a broader range of cell types. Constitutive signaling activity, which is exhibited by some native GPCRs (Milano et al. 1994), has been observed more commonly with mutated GPCRs (Lefkowitz et al. 1993; Alblas et al. 1996) in an increasing number of human diseases, including tumors (Coughlin 1994; Sande et al. 1995). Finally, the enhanced proliferation exhibited by KSHV GPCR transfectants supports a role for this receptor in tumorigenesis.

The presence of this functional, constitutively active GPCR in the genome of a virus that is so tightly associated with specific malignancies provides circumstantial evidence toward its pathogenetic role. Two alternative, or perhaps complementary, hypotheses can be proposed to explain the role of the viral GPCR in the development of KSHV-associated diseases: a direct mechanism, in which the constitutive signaling activity of KSHV GPCR leads to altered growth and neoplastic transformation, and/or an indirect mechanism, where signaling by KSHV GPCR induces the expression of other genes which are in turn involved in pathogenetic events. For example, the latter model could apply to the case of basic fibroblast growth factor (bFGF) which has previously been shown to play a pivotal role in the development of KS lesions (Ensoli et al. 1989), and whose expression is driven by an AP-1 binding, and probably PKC-responsive promoter (Erdos et al. 1995).

The determination of the effect on cells expressing HHV 8 GPCRs of negative antagonists of HHV 8 GPCRs will delineate the role(s) of HHV 8 GPCRs in infected cells. In this regard, the two most important downstream effects are the stimulation of cell proliferation or if HHV 8 GPCR activity caused cell transformation. One can determine whether HHV 8 GPCR can induce cell transformation and whether antagonists can inhibit this effect. Transformation in NIH 3T3 fibroblasts can be used in a protocol used to show that the agonist-activated serotonin 1c receptor, another GPCR, is capable of triggering transformation (Julius et al. 1989). In this assay, HHV 8 GPCR expression will be produced by transfection with plasmids encoding HHV 8 GPCR, not by infection with HHV-8. This assay will show whether HHV 8 GPCR expression leads to a transformed phenotype and provide a quantitative assessment of the effect of antagonist on transforming activity of HHV 8 GPCR because the number of foci of transformed cells in the absence versus the presence of antagonist can be counted. One can also determine whether HHV-8 infection will transform $CD19^+$ B-cells in experiments similar to those performed to show lymphoblastoid transformation by Herpesvirus saimiri and Epstein-Barr viruses (Rangan et al. 1977; Miller 1974). If this series of experiments shows that HHV 8 GPCR expression causes transformation in these in vitro assays, one can determine whether cells from these foci will generate tumors in nude mice and whether this can be inhibited by antagonists.

B-cell lines will be used for studies of cell proliferation because of ease of their experimental manipulation. These B-cell lines may not be good models for study of proliferation because they may have acquired other changes (mutations) that allow them to proliferate without the signalling activity of HHV 8 GPCRs. Acutely infected cells, such as B-cells, will be used and one can study other cell lines including human lymphoblastoid cell lines UH-1 and CB-33, and endothelial and fibroblast cell lines derived from KS lesions. An effect of antagonists of HHV 8 GPCR to inhibit the rates of cell proliferation will be monitored. This will be tested in a standard assay by measuring the rate of proliferation of cells incubated without (control) and with antagonists. By counting cells, which are seeded at low density, over time, one can determine the effect of these antagonists on the generation times of these cells. Different incubation mediums can be tested and, in particular, attempt to adjust the type and concentration of the serum supplement so that there is a moderate generation time for cells in the absence of antagonists. This will allow for the highest likelihood of observing an inhibitory effect on proliferation. These experiments will be complemented with those that measure DNA synthesis more directly, for example, by measuring [$^3$H]thymidine incorporation into DNA and by measuring DNA content, for example with 5-bromodeoxyuridine. The most definitive measurement of cell proliferation is, however, the rate of increase in cell number over time.

These experiments will establish whether HHV 8 GPCR is expressed at the protein level in infected cells, whether HHV 8 GPCR stimulates cellular transformation and/or proliferation and whether the negative antagonists discovered according to the method of the subject invention will inhibit these effects.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Ahuja, S. K., and Murphy, P. M., *J Biol Chem* 268:20691–20694 (1993).
Alblas, J., et al., *EMBO J* 15:3351–3360 (1996).
Allen, L. F., et al., *Proc Natl Acad Sci USA* 88:11354–11358 (1991).
Arvanitakis, L., et al., *Blood* 88:2648–2654 (1996).
Baggiolini, M., et al., *Adv Immunol* 55:97–179 (1994).
Baldwin, J. M., *EMBO J* 12:1693–1703 (1993).
Baldwin, J. M., *Curr Opin Cell Biol* 6:180–190 (1994).
Barker, E. L., et al., *J Biol Chem* 269:11687–11690 (1994).
Cesarman, E., et al., *N Eng J Med* 332:1186–1191 (1995).
Cesarman, E., et al., *J Virol* 70:8218–8223 (1996).
Chang, Y., et al., *Science* 266:1865–1869 (1994).
Chidiac, P., et al., *Mol Pharmacol* 45:490–499 (1994).
Costa, T., and Herz, A., *Proc Natl Acad Sci USA* 86:7321–7325 (1989).
Costa, T., et al., *Mol Pharmacol* 41:549–560 (1992).
Coughlin, S. R., *Curr Opin Cell Biol* 6:191–197 (1994).
Dotto, G. P., et al., *Nature* 318:472–475 (1985).
Ensoli, B., et al., *Science* 243:223–226 (1989).
Erdos, G., et al., *J Cell Physiol* 164:404–413 (1995).
Gershengorn, M. C., and Perlman, J. H., in *Endocrinology*, 3d Edition, L. J. DeGroot, Ed., W. B. Saunders Co., Philadelphia, Pa., pp. 66–76 (1995).
Gutkind, J. S., et al., *Proc Natl Acad Sci USA* 88:4703–4707 (1991).
Habener, J., in *Endocrinology*, 3d Edition, L. J. DeGroot, Ed., W. B. Saunders Co., Philadelphia, Pa., pp. 77–92 (1995).
Hasegawa, H., et al., *J Biol Chem* 271:1857–1860 (1996).
Holmes, W. E., et al., *Science* 253:1278–1280 (1991).
Julius, D., et al., *Science* 244:1057–1062 (1989).
Karin, M., *J Biol Chem* 270:16483–16486 (1995).
Leeb-Lundberg, L. M. F., et al., *J Biol Chem* 269:25970–25973 (1994).
Lefkowitz, R., et al., *Trends Pharmacol Sci* 14:303–307 (1993).
Loyter, A., et al., *Proc Natl Acad Sci USA* 79:422–426 (1982).
Matus-Leibovitch, N., et al., *J Biol Chem* 270:1041–1047 (1995).
Milano, C. A., et al., *Science* 264:582–586 (1994).
Miller, G., *J Infect Dis* 130:187–205 (1974).
Moore, P. S., and Chang, Y., *N Eng J Med* 332:1181–1185 (1995).
Moore, P. S., et al., *J Virol* 70:549–558 (1996).
Murphy, P. M., and Tiffany, H. L., *Science* 253:1280–1283 (1991).
Nanevicz, T., et al., *J Biol Chem* 270:21619–21625 (1995).
Navia, M. A., and Murcko, M. A., *Curr Opin Struct Biol* 2:202–210 (1992).
Nicholas, J., et al., *Nature* 355:362–365 (1992).
Nussenzveig, D. R., et al., *J Biol Chem* 268:2389–2392 (1993).
Nussenzveig, D., et al., *J Biol Chem* 269:28123–28129 (1994).
Pei, G., et al., *Proc Natl Acad Sci USA* 91:2699–2702 (1994).
Rangan, S. R., et al., *J Natl Cancer Inst* 59:165–171 (1977).
Ren, Q., et al., *J Biol Chem* 268:16483–16487 (1993).
Roizman, B., in *Fields Virology*, eds. Fields, B. N., Knipe, D. M., and Howley, P. M., pp. 2221–2231, Lippincott-Raven, Philadelphia (1996).
Samama, P., et al., *J Biol Chem* 268:4625–4636 (1993).
Samama, P., et al., *Mol Pharmacol* 45:390–394 (1994).
Sambrook, J., et al., *Molecular Cloning: A Laboratory Manual*, Cold Spring Harbor Press, Cold Spring Harbor, N.Y. (1989).
Sande, J. V., et al., *J Clin Endocrinol Metab* 80:2577–2585 (1995).
Schadlow, V., et al., *Mol Biol Cell* 3:941–951 (1992).
Schutz, W., and Freissmuth, M., *Trends Pharmacol Sci* 13:376–380 (1992).
Sciacca, F. L., et al., *J Immunol* 153:4816–4825 (1994).
Straub, R., et al., *Proc Natl Acad Sci USA* 87:9514–9518 (1990).
Tiberi, M., and Caron, M. G., *J Biol Chem* 269:27925–27931 (1994).
Van Rhee, A. M., and Jacobson, K. A., *Drug Dev Res* 37:1–38 (1996).
Vassart, G., et al., *Ann NY Acad Sci* 766:23–30 (1995).
Wu, D., et al., *Science* 261:101–103 (1993).
Young, D., et al., *Cell* 45:711–719 (1986).
Zhou, W., et al., *Mol Pharmacol* 45:165–170 (1994).

What is claimed is:

1. A method of identifying a negative antagonist of a constitutively active G protein coupled receptor of human herpesvirus 8, said method comprising:

co-expressing in a host cell a constitutively active G protein coupled receptor of human herpesvirus 8 and a reporter protein, wherein expression of the reporter protein is controlled by a promoter responsive to a signaling pathway activated by the constitutively active G protein coupled receptor of human herpesvirus 8;

determining a first activity level of the reporter protein;

exposing the host cell to a test substance;

determining a second activity level of the reporter protein after said exposing the host cell to the test substance; and identifying the test substance, where the second activity level is less than the first activity level, as a negative antagonist of the constitutively active G protein coupled receptor of human herpesvirus 8.

2. The method of claim 1 wherein said promoter is a cyclic AMP-responsive promoter.

3. The method of claim 1 wherein said promoter is a protein kinase C-responsive promoter.

4. The method of claim 1 wherein said reporter protein is luciferase.

5. The method of claim 4 wherein said determining the first and second activity levels is carried out using a luminescent assay.

6. The method of claim 1 wherein said host cell is a mammalian cell.

7. The method of claim 6 wherein said mammalian cell is a COS cell.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 342 amino acids
      (B) TYPE: amino acid
      (C) STRANDEDNESS:
      (D) TOPOLOGY: linear -continued (ii) MOLECULE TYPE: protein (xi) SEQUENCE DESCRIPTION: SEQ ID NO:1:

```
Met Ala Ala Glu Asp Phe Leu Thr Ile Phe Leu Asp Asp Glu Ser
1               5                   10                  15

Trp Asn Glu Thr Leu Asn Met Ser Gly Tyr Asp Tyr Ser Gly Asn Phe
                20                  25                  30

Ser Leu Glu Val Ser Val Cys Glu Met Thr Thr Val Val Pro Tyr Thr
                35                  40                  45

Trp Asn Val Gly Ile Leu Ser Leu Ile Phe Leu Ile Asn Val Leu Gly
    50                  55                  60

Asn Gly Leu Val Thr Tyr Ile Phe Cys Lys His Arg Ser Arg Ala Gly
65                      70                  75                  80

Ala Ile Asp Ile Leu Leu Leu Gly Ile Cys Leu Asn Ser Leu Cys Leu
                85                  90                  95

Ser Ile Ser Leu Leu Ala Glu Val Leu Met Phe Leu Phe Pro Asn Ile
                100                 105                 110

Ile Ser Thr Gly Leu Cys Arg Leu Glu Ile Phe Phe Tyr Tyr Leu Tyr
                115                 120                 125

Val Tyr Leu Asp Ile Phe Ser Val Val Cys Val Ser Leu Val Arg Tyr
            130                 135                 140

Leu Leu Val Ala Tyr Ser Thr Arg Ser Trp Pro Lys Lys Gln Ser Leu
145                 150                 155                 160

Gly Trp Val Leu Thr Ser Ala Ala Leu Leu Ile Ala Leu Val Leu Ser
                    165                 170                 175

Gly Asp Ala Cys Arg His Arg Ser Arg Val Val Asp Pro Val Ser Lys
                180                 185                 190

Gln Ala Met Cys Tyr Glu Asn Ala Gly Asn Met Thr Ala Asp Trp Arg
                195                 200                 205

Leu His Val Arg Thr Val Ser Val Thr Ala Gly Phe Leu Leu Pro Leu
        210                 215                 220

Ala Leu Leu Ile Leu Phe Tyr Ala Leu Thr Trp Cys Val Val Arg Arg
225                 230                 235                 240

Thr Lys Leu Gln Ala Arg Arg Lys Val Arg Gly Val Ile Val Ala Val
                    245                 250                 255

Val Leu Leu Phe Phe Val Phe Cys Phe Pro Tyr His Val Leu Asn Leu
                260                 265                 270

Leu Asp Thr Leu Leu Arg Arg Arg Trp Ile Arg Asp Ser Cys Tyr Thr
            275                 280                 285

Arg Gly Leu Ile Asn Val Gly Leu Ala Val Thr Ser Leu Leu Gln Ala
    290                 295                 300

Leu Tyr Ser Ala Val Val Pro Leu Ile Tyr Ser Cys Leu Gly Ser Leu
305                 310                 315                 320

Phe Arg Gln Arg Met Tyr Gly Leu Phe Gln Ser Leu Arg Gln Ser Phe
                325                 330                 335

Met Ser Gly Ala Thr Thr
                340
```